United States Patent [19]

Erker

[11] Patent Number: 4,464,776
[45] Date of Patent: Aug. 7, 1984

[54] MULTIPLEXING SIGNAL PROCESSING CHANNELS IN A CT SCANNER WITH ROTATING SOURCE

[75] Inventor: Joseph W. Erker, Aurora, Ohio
[73] Assignee: Technicare Corporation, Solon, Ohio
[21] Appl. No.: 507,187
[22] Filed: Jun. 23, 1983
[51] Int. Cl.³ .......................... A61B 6/00; G03B 41/16
[52] U.S. Cl. ........................................ 378/010; 378/19
[58] Field of Search .................................. 378/10, 19

[56] References Cited

U.S. PATENT DOCUMENTS 4,220,863 9/1980 McBride et al. ...................... 378/19

Primary Examiner—Alfred E. Smith
Assistant Examiner—T. N. Grigsby
Attorney, Agent, or Firm—Michael A. Kaufman

[57] ABSTRACT

A CT scanner having an outer circular array of stationary radiation detectors for an inner concentrically revolving source of radiation emitted in a fan pattern subtending a number of the detectors. Each grouping of 15 consecutive detectors is housed in a detector module, each one of which is provided with an electro-optical device which is arranged to normally deactivate the output of each of the detectors in the module. The detectors are arranged in exclusive groups of four nonconsecutive detectors each equiangularly disposed about the array connected in daisy chain fashion with the output of each of said nonconsecutive detector groups applied to a single signal cable defining a corresponding signal processing channel. There is also provided an opaque vane arranged for rotation in fixed relation to said revolving source of radiation for temporarily interrupting the deactivation caused by each of the electro-optical devices which correspond to those detectors in the array which at any time are being irradiated by said source.

10 Claims, 8 Drawing Figures

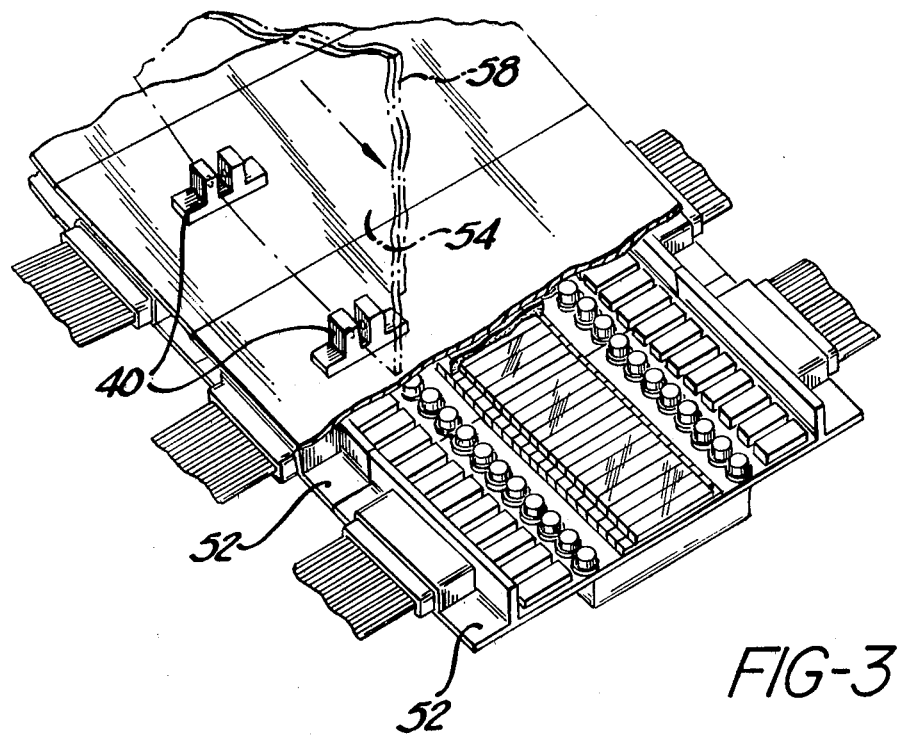
FIG-3
FIG-4
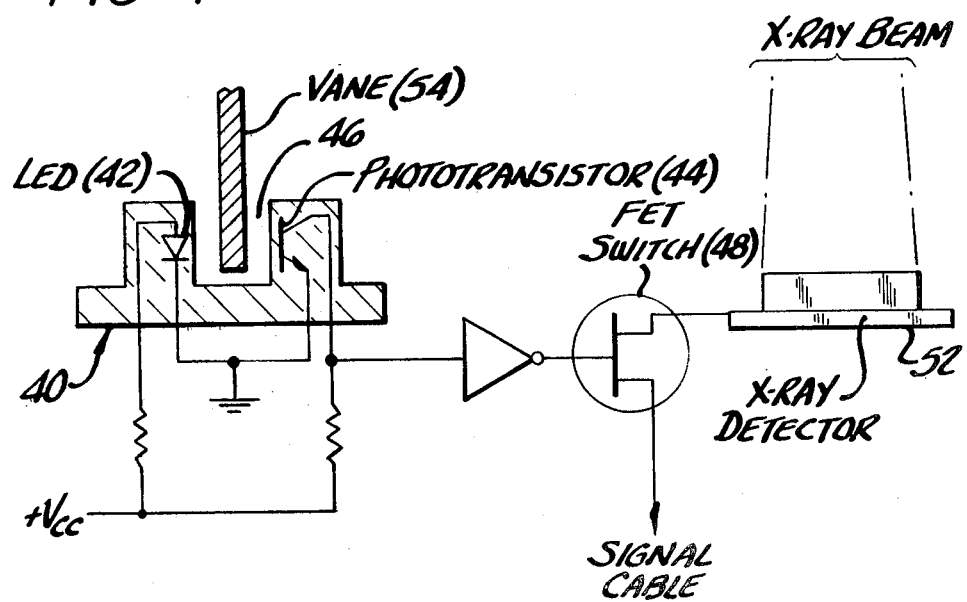

MULTIPLEXING SIGNAL PROCESSING CHANNELS IN A CT SCANNER WITH ROTATING SOURCE

TECHNICAL FIELD

This invention relates generally to the field of radiation imaging of internal structures and more specifically to computerized transaxial tomography (CT) X-ray scanners.

BACKGROUND OF THE INVENTION

As is now well known, the CT scanner produces narrow beams of radiation, typically x-radiation, through plural coplanar paths defining a cross-sectional or tomographic view of a patient's internal organs, such as the brain or the thoracic region. The attenuated beams are sensed by radiation detectors whose electrical output is indicative of the intensity of the radiation received by the detector. The electrical output of each of these detectors is passed to a signal processing channel and the data acquired by these channels is reconstructed and eventually displayed.

During the approximate 10 years of their existence, CT scanners have undergone several generations of change, each of which has been accompanied by a marked increase in the number of detectors. The architecture in use today which makes use of the greatest number of detectors employs a rotating fan beam source with a stationary arc of uniformly spaced detectors about the center point of a scan circle. The fan beam source revolves about the center point inside the detector array irradiating the scan circle and subtending at any given time only a fraction of the detectors in the total array. If desired, the array may be a complete circle or ring. In an arrangement of the above-described type, the stationary array of spaced detectors may number several hundred or more. As the number of detectors increases, it becomes more and more cumbersome to provide each detector in the array with a respective exclusive signal processing channel.

In U.S. Pat. No. 4,220,863 to McBride, et al., a data channel multiplexing system is taught for use with a 720 detector CT scanner which requires only 180 channels of signal processing electronics. In the McBride, et al. system a number of signal processing channels—180 in one embodiment—corresponding to the maximum number of detectors subtended by the fan pattern at any time is connected by switching circuitry to receive the outputs of only the irradiated detectors. This is accomplished by providing a shift register, including a series of detector bits, initially loading a predetermined number (e.g., all "ones") into a series of consecutive bits corresponding to the maximum number of detectors subtended by the radiation fan. The shift register bits are then clocked or shifted collectively each time the source advances so that it irradiates another peripheral detector. A number of gates comprising switching circuitry corresponding to the maximum number of detectors subtended by the fan pattern is connected to receive the outputs of a respective exclusive group of nonconsecutive detectors, one and only one of which is irradiated at any given time by the radiation fan. For any given position of the source, each gate permits the passage of the output of only the one irradiated detector as determined by the state of the shift register detector bits corresponding respectively to the detectors in the group received by the particular gate.

SUMMARY OF THE INVENTION

I have invented a new multiplexing system which accomplishes the same savings in the number of signal processing channels in a CT scanner as in the above-described McBride, et al. patent, but without the need for sophisticated electronic switching circuitry to insure the passage of the output of only one detector per data channel at any given time. In the data channel multiplexing system according to the present invention, the outputs of an exclusive group of nonconsecutive detectors in the array are interconnected so that only one in each group is irradiated in any given time by the radiation fan.

In a preferred embodiment, there are four connected detectors in each exclusive group, each being 90° separated from its two adjacent neighbors. To be sure that the output signals of only one detector in each such connected group is permitted to transmit its output signal at any given time, the output signals of all detectors are normally switched off. In the preferred embodiment, the CT scanner includes 1,440 detectors arranged in 96 modules of 15 detectors each. Each of these modules is provided with an electro-optical device that includes a light emitting diode and a photosensitive transistor separated by an air gap. The photosensitive transistor is connected to an electronic switch that controls the passage of the output of 15 detectors. The photosensitive transistor controls the state of the output signal switch forcing it to be turned off as long as the phototransistor is illuminated by the light emitting diode, thereby preventing the passage of the output signals of its associated 15 detectors.

To permit the output signals of all detectors irradiated at any given time by the radiation fan to pass, there is provided means rotatable about said patient scan circle in fixed relation with said rotating source for temporarily changing the state of the output signal switch. Thus, all detectors subtended by the fan pattern at any given time are permitted to transmit their output signals to their corresponding signal processing channel. In a preferred embodiment, this is accomplished by an opaque vane which passes through the air gaps of several of these electro-optical devices interrupting the light beam to the phototransistor and causing the output signal switch to be turned on. The vane is mounted on the rotating member of the CT scanner, opposite the source of radiation. As the radiation source rotates about the scan circle, only those detectors whose electro-optical devices are deactivated by the vane are turned on, all others are maintained off.

BRIEF DESCRIPTION OF THE DRAWINGS

FIG. 3 is an enlarged detail illustrating several of the detector modules of FIG. 2.

FIG. 4 is a schematic diagram illustrating an opaque vane interposed between an electro-optical device controlling one of the detector modules in accordance with the present invention.

DETAILED DESCRIPTION OF THE PREFERRED EMBODIMENTS INCLUDING THE BEST MODE

Figure 1:
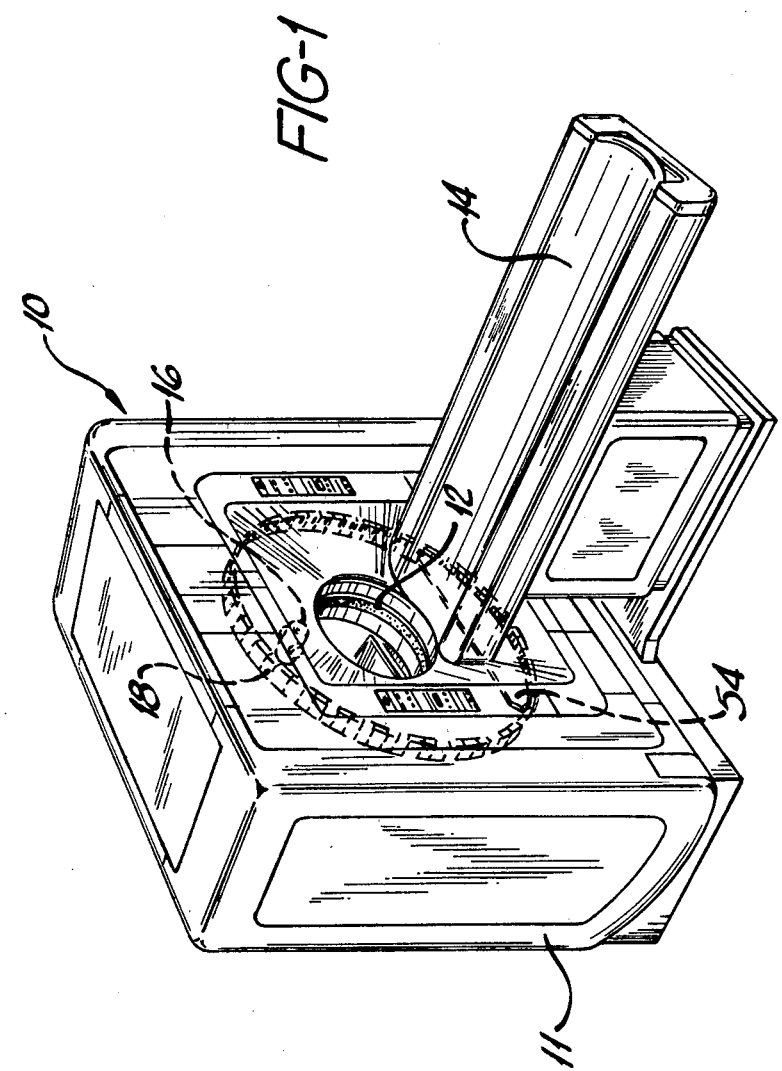
FIG. 1 is a perspective view of a CT scanner assembly in accordance with the present invention arranged in modules having a stationary ring of radiation detectors.

FIG. 1 illustrates the mechanical apparatus associated with a rotating source type CT scanner system. A gantry assembly 10 is shown having a tiltable frame 11 and a central circular opening 12 through which a patient is inserted for a body scan, for example, on patient table 14. Shown in phantom, rotating source 16 produces radiation in a coplanar fan beam pattern directed towards the opposite side of the opening 12. Mechanism within the gantry assembly rotate the source 16 alternately clockwise and counterclockwise about an axis through the center of the opening 12 perpendicular to the fan beam. A ring of detectors 18, also shown in phantom in FIG. 1, is disposed within the frame 11 concentrically about the opening 12 and at a somewhat greater radius from the center of the opening 12 than the source 16. The detector ring 18 lies in the same plane as the fan beam.

Figure 5A:
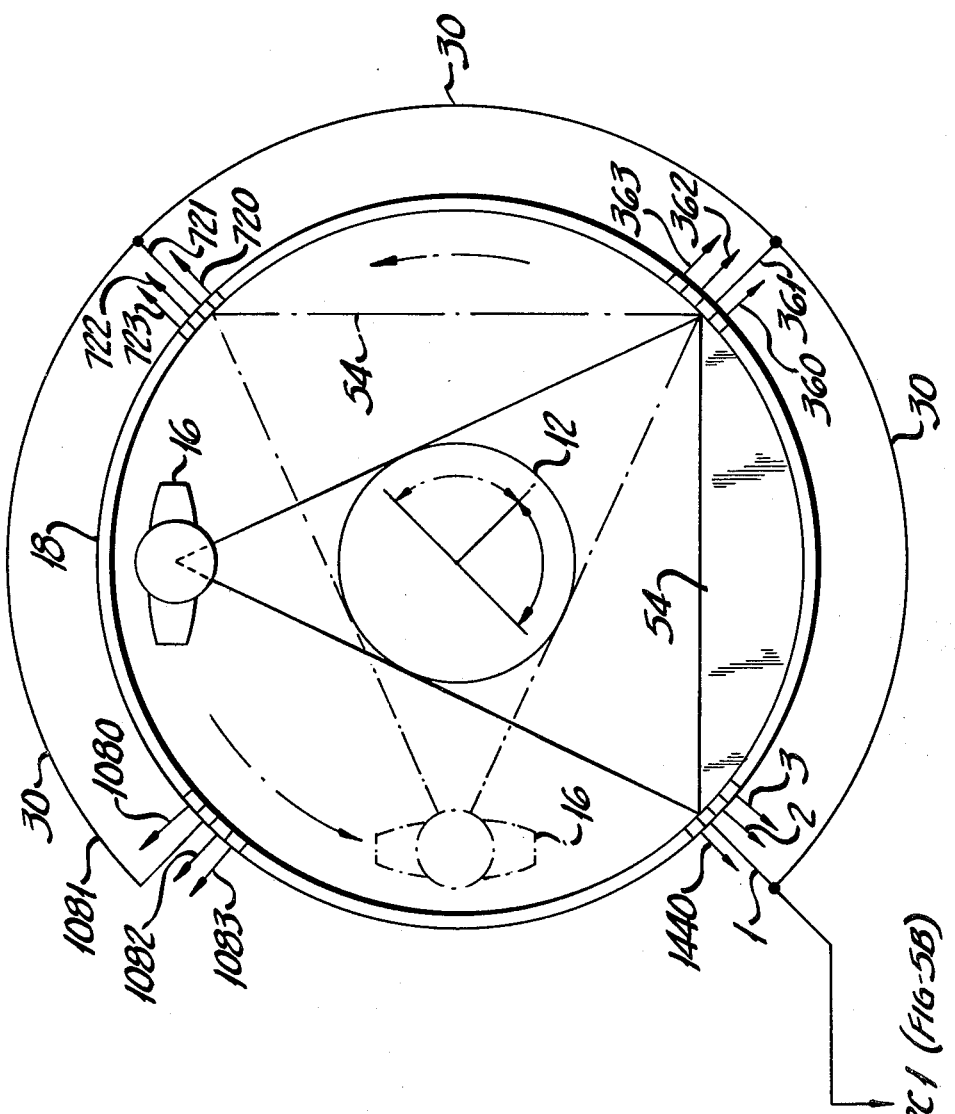
FIGS. 5B and 5A are block and schematic diagrams respectively of the signal processing channel multiplexing system for a rotating source type CT scanner according to the invention.
Figure 5B:
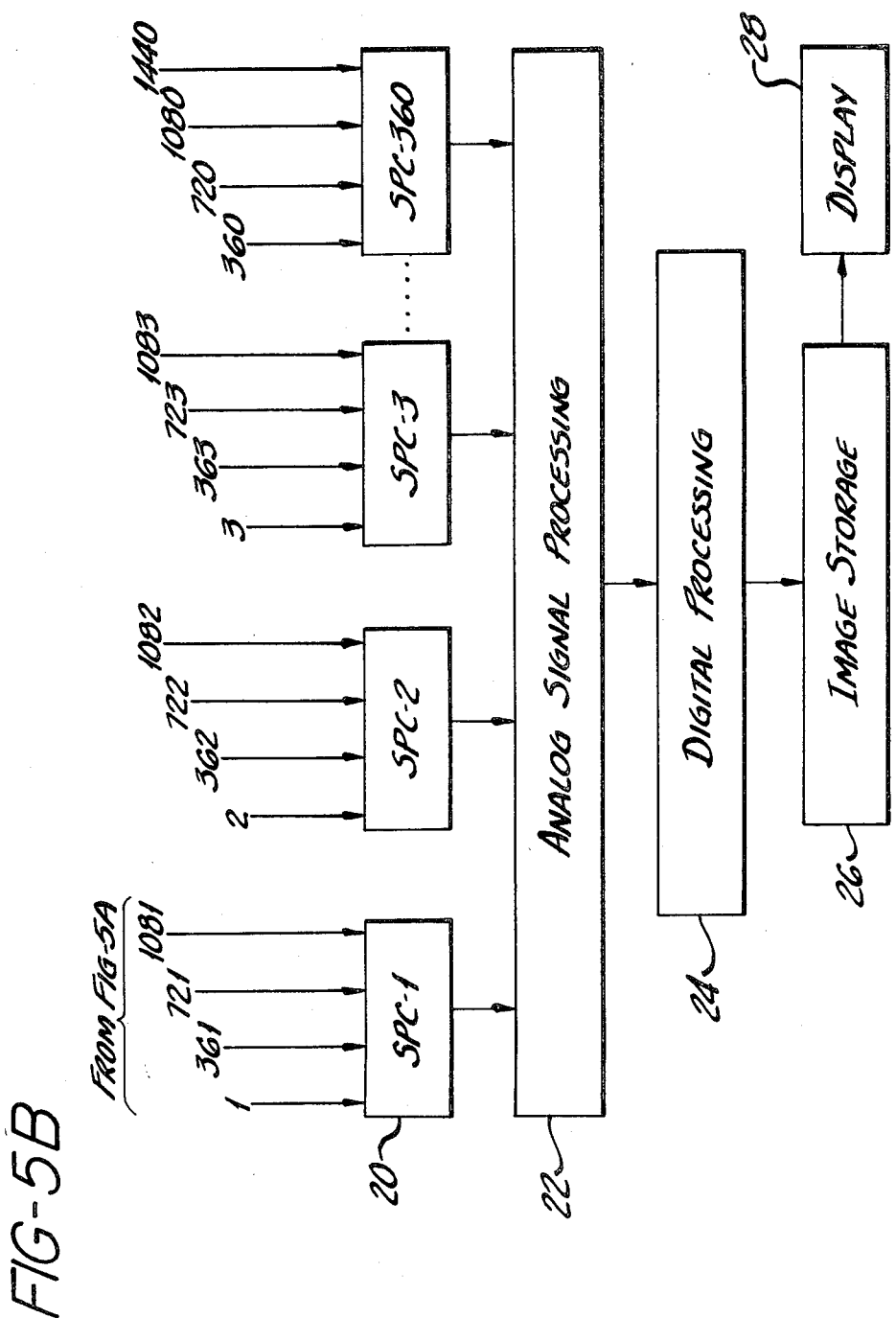

FIG. 5 shows a system having a full compliment of 1,440 detectors spaced at one-fourth degree intervals around the detector ring 18. Only certain ones of the detectors are indicated schematically for convenience. Beginning in the middle of the lower left-hand quadrant of the detector ring, as viewed in FIG. 5, the detectors are numbered consecutively, counterclockwise, from 1 to 1,440. The rotating source 16 is shown in its initial position at the start of a scan. The fan beam width of the radiation produced by the source 16 is adjustable to accommodate a variety of scan circle diameters, but is arranged so that under no circumstances will it subtend greater than 90° of arc of the detector ring 18. Thus, the fan beam will never irradiate at one time more than 360 detectors or one-fourth of the total. A mechanism for adjusting the angle of the fan beam emitted by source 16 to accommodate different size scan circles is disclosed in U.S. Pat. No. 4,277,685 to Kovic, et al. In the scanner shown in FIG. 1, a 40 centimeter diameter scan circle results in 63° of the detector ring 18 being irradiated at one time, while a 50 centimeter diameter scan circle, the maximum provided in applicant's best mode, results in just under 80° of the detector ring being irradiated at one time corresponding to approximately 320 detectors, less than one-fourth of the total.

Since at any given position of the source 16, only a fraction of the full compliment of detectors is producing meaningful data, there is no need to process the signals from the nonirradiated detectors at the same time. Even with the largest available scan circle, no more than one-fourth of the detectors need be processed at one time. Thus, to process the signals from all active detectors, of the 1,440 total, 360 channels of signal processing electronics are always sufficient.

360 identical signal processing channels 20 are provided for a corresponding analog signal processing system 22. The output is digitized and passed for digital processing into reconstructed image data and digital processing system 24. The reconstructed image data is stored in image storage 26 which is ultimately read out to a convenient display 28.

Access to each signal processing channel 20 is shared by four corresponding detectors whose outputs are connected by a single signal cable 30. In the preferred embodiment, each signal processing channel 20 receives outputs from four detectors spaced 90° from each other. For example, signal processing channel 1 is connected to receive simultaneously the outputs of detectors 1, 361, 721, and 1,021. Signal processing channel 2 is connected to receive the outputs of detectors 2, 362, 722, and 1,082. Signal processing channel 3 is connected to receive the outputs of detectors 3, 363, 723, and 1,083 and so on up to signal processing channel 360 which is connected to receive the outputs of detector 360, 720, 1,080, and 1,440. The required number of signal processing channels depends on the maximum number of detectors subtended during a scan of the largest size scan circle available. For example, if there is a full compliment of detectors spaced about 360° of arc, and the radiation fan never subtends more than p detectors, there will be at least p signal processing channels 20. In the preferred embodiment, even though there are at most 320 detectors subtended at one time, 360 signal processing channels are provided since the maximum number of detectors which can be connected together with 320 detectors being irradiated at one time is four. To permit detectors to be connected in sets of five would limit to no more than 288 detectors (one-fifth of 1,440) from being subtended at any one time. Under such an arrangement, no more than one-fifth of the detector ring or 72° (one-fifth of 360°) could be irradiated at one time.

Since the outputs of several detectors are connected together before being applied to one signal processing channel, a technique is required to deactivate the outputs of all detectors except the one being irradiated. This is accomplished by deactivating means such as a disabling or switching mechanism shown in FIG. 4 which ensures that the output signal of each detector is normally switched off. There is shown in FIG. 4 an electro-optical device 40 which includes a light emitting diode (LED) 42 and an optically coupled photosensitive transistor 44 separated from LED 42 by an air gap 46. In conventional fashion, the LED 42 is provided with a power source $V_{cc}$ to provide a light output that travels across the air gap 46 onto the base of the phototransistor 44. The light exposure to the base of the phototransistor 44 results in an increased collector current which is applied to an electronically controlled switch such as FET 48 through an amplifier 50. The application of this current results in the FET switch 48 becoming nonconducting so that the output of each X-ray detector connected to the FET switch 48 is not permitted to be passed to its associated signal cable 30.

Due to the very high number of detectors (1,440) in the scanner shown in FIG. 1, every fifteen detectors are grouped together in a detector module 52 as shown in FIG. 3 with one electro-optical device 40 being provided for each. Thus, a single electro-optical device 40 controls the passage of the output signal of each of the fifteen detectors in the grouping.

Figure 6:
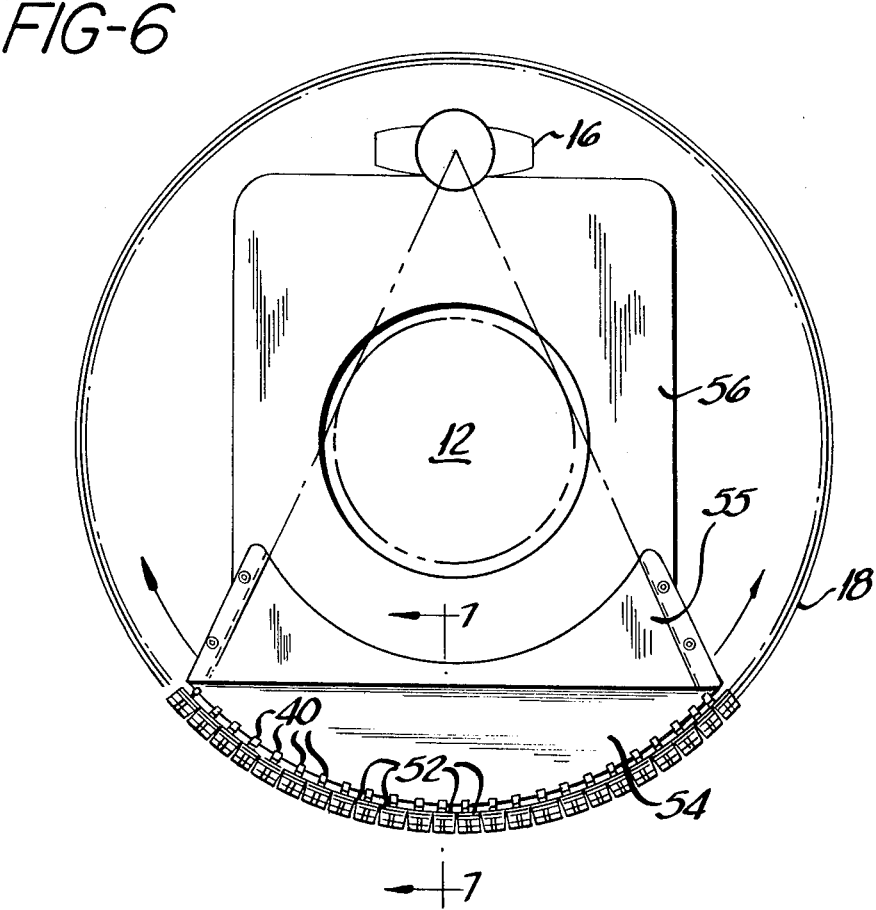
FIG. 6 is an elevational view, partially schematic, showing the opaque vane attached to the CT scanner.

Whenever the air gap 46 is interrupted so that light emitted by LED 42 is not detected by phototransistor 44 the collector current decreases. This reverses the bias on the FET switch 48, placing it in a conducting mode, thereby permitting the output signal of each X-ray detector connected to the switch to be passed to that detector's associated signal cable. The interruption of the light passage between LED 42 and phototransistor 44 in the preferred embodiment is provided by deactivating means such as an opaque vane 54 a portion of which passes through air gap 46. As shown in FIG. 6, the vane 54 is mounted for rotation with the radiation source 16 on the detector side of the scanner. The vane is conveniently attached to a detector side collimator 55 which is also rotatable since it, in turn, is attached to a rotating member 56 on which the source 16 is mounted.

Figure 7:
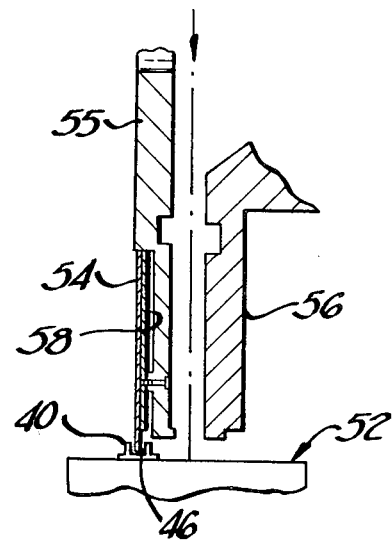
FIG. 7 is a section taken along lines 7—7 of FIG. 6.

As shown in FIG. 7, the vane 54 has a laminate construction with a frontal portion 57 mounted on a backing plate 58. The frontal portion extends further than the backing plate 58 and alone protrudes into the air gap 46.

Figure 2:
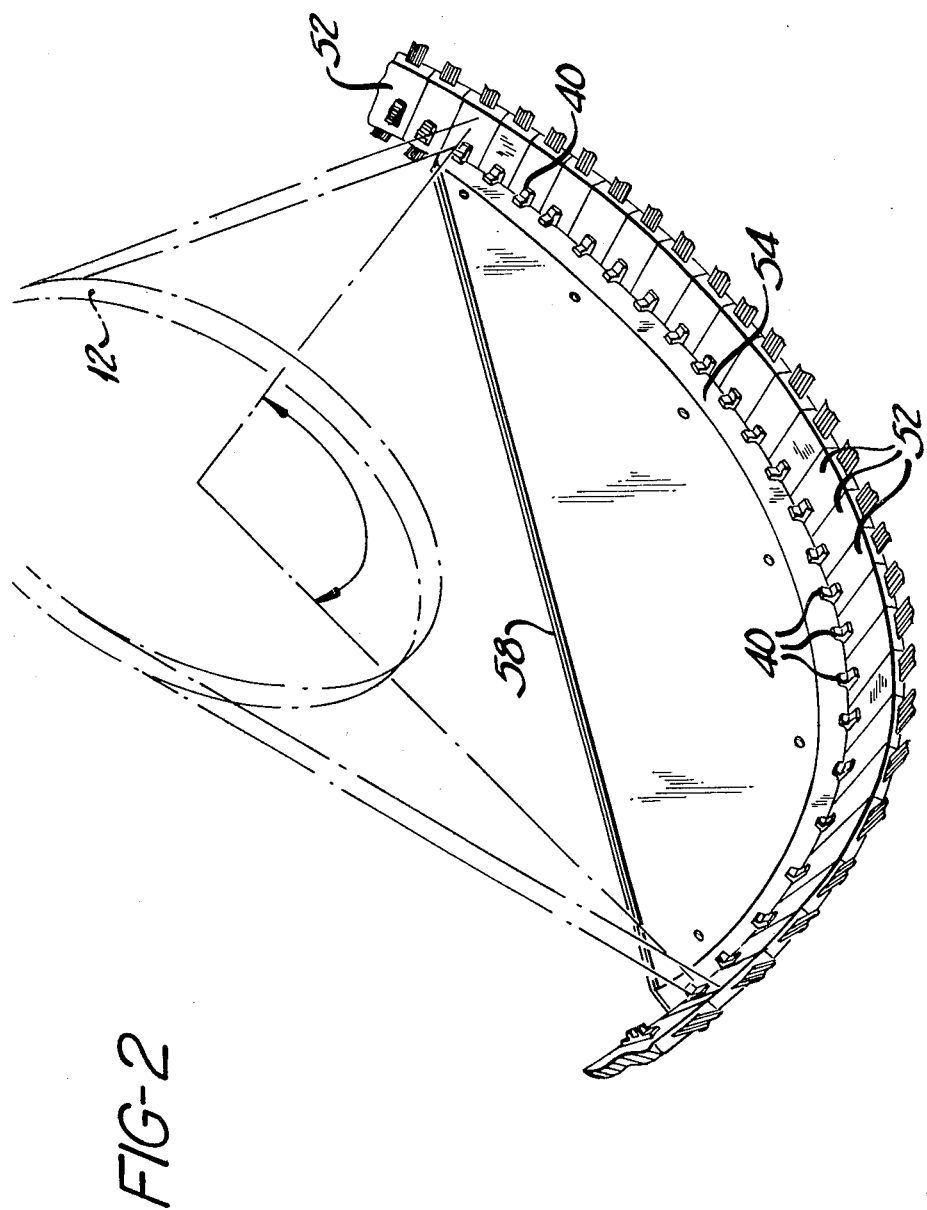
FIG. 2 is a perspective view showing a portion of the array of detector modules.

As illustrated in FIG. 2, the arc length of the opaque vane 54 is equal to the arc length of the widest radiation fan beam and hence always turns on every electro optical device 40 that corresponds to the array of detectors that are at any given time irradiated. Thus, even though each signal processing channel 20 connects the outputs of four separate detectors, the outputs of at least three of these detectors is always shut off by an FET switch 48 and only the output of that detector whose output is permitted to be passed is applied to the signal processing channel.

I claim:

1. In a CT scanner having an array of stationary radiation detectors spaced in a curved path about a center point and having a concentrically rotating source of radiation emitted in a fan pattern subtending a number of the detectors, each detector producing an electronic output signal having an amplitude indicative of the intensity of radiation impinging upon that detector, the irradiated area common to different positions of the fan pattern defining a corresponding patient scan circle, a data channel multiplexing system which comprises:
   (a) a number of signal collecting means corresponding to at least the maximum number of detectors subtended by the fan pattern, each such signal collecting means connected to receive the electronic output signals of a respective exclusive group of nonconsecutive detectors, one and only one of which is irradiated at any given time by the radiation fan, for passing the electronic output signal at one time of no more than one detector in each group, the output of each said collecting means defining a corresponding signal processing channel;
   (b) a plurality of deactivating means each associated with a grouping of one or more detectors, for normally deactivating the output signal of each detector in said group; and
   (c) means, rotatable about said patient scan circle in fixed relation with said rotating source of radiation, for temporarily interrupting the deactivation means associated with a number of groups of adjacent detectors corresponding generally to the detectors subtended by the fan pattern to permit coupling to said signal collecting means the outputs of those adjacent detectors which at any time are subtended by said fan beam of radiation.

2. In the system of claim 1 wherein one of said deactivating means includes a light emitting diode and a phototransistor separated by an air gap and optically connected to said light emitting diode.

3. In the system of claim 2 wherein one of said deactivating means further includes an electronically controlled switch connected to the group of detectors associated with said deactivating means wherein said switch has two electronic states, only one of which permits passage of the outputs of the detectors in said group to their respective signal collecting means.

4. In the system of claim 3 wherein said switch is an FET.

5. In the system of claim 2 wherein said means for temporarily interrupting the deactivating means is an opaque vane that passes within the air gap of each deactivating means as it rotates about said patient scan circle.

6. In the system of claim 1 wherein each detector in a respective exclusive group of nonconsecutive detectors is disposed equiangularly about the center point in the array of stationary detectors.

7. In the system of claim 6 wherein said array comprises 1,440 detectors, and there are 360 signal collecting means each connected to receive the electronic output signals of a respective exclusive group of four nonconsecutive detectors.

8. In the system of claim 1 wherein said scanner has an array of 1,440 stationary radiation detectors arranged in 96 detector modules each one of which includes a group of 15 detectors wherein each module is associated with one of said deactivating means.

9. In the system of claim 1 wherein said CT scanner has an array of 1,440 stationary radiation detectors, there are 360 signal collecting means each connected to receive the electronic output signals of a respective exclusive group of four nonconsecutive detectors spaced at 90° intervals about the curved path of said detectors, wherein the detectors are arranged in 96 groups of 15 each, each one of said 96 groups being associated with one of said deactivating means.

10. In the system of claim 9 wherein each of said deactivating means includes a light emitting diode, a phototransistor separated from said light emitting diode by an air gap and optically connected to said light emitting diode, the output of said phototransistor being applied to an electronic switch having a conducting and a nonconducting state wherein reception of light by said phototransistor biases said switch into one of its states while interruption of light reception by that phototransistor serves to change the state of said switch.

* * * * *